US009149417B2

(12) United States Patent
Lokken

(10) Patent No.: US 9,149,417 B2
(45) Date of Patent: Oct. 6, 2015

(54) TOOTH WHITENING PRODUCTS AND METHODS OF MAKING THE SAME

(75) Inventor: Jeffrey J. Lokken, Buffalo, NY (US)

(73) Assignee: Lornamead Brands, Inc., Tonawanda, NY (US)

( * ) Notice: Subject to any disclaimer, the term of this patent is extended or adjusted under 35 U.S.C. 154(b) by 1647 days.

(21) Appl. No.: 12/202,747

(22) Filed: Sep. 2, 2008

(65) Prior Publication Data

US 2008/0317797 A1    Dec. 25, 2008

Related U.S. Application Data

(63) Continuation of application No. 10/975,064, filed on Sep. 22, 2004.

(30) Foreign Application Priority Data

Jun. 9, 2004  (CA) ...................................... 2470463

(51) Int. Cl.
    *A61K 8/22*       (2006.01)
    *A61Q 11/00*      (2006.01)
    *A61K 8/02*       (2006.01)
    *A61C 19/06*      (2006.01)
    *A61K 8/73*       (2006.01)

(52) U.S. Cl.
    CPC ............. *A61K 8/0208* (2013.01); *A61C 19/063* (2013.01); *A61C 19/066* (2013.01); *A61K 8/22* (2013.01); *A61K 8/731* (2013.01); *A61Q 11/00* (2013.01)

(58) Field of Classification Search
    None
    See application file for complete search history.

(56) References Cited

U.S. PATENT DOCUMENTS

| | | | |
|---|---|---|---|
| 5,077,047 A | 12/1991 | Biss et al. | |
| 5,879,691 A | 3/1999 | Sagel et al. | |
| 5,891,453 A | 4/1999 | Sagel et al. | |
| 5,894,017 A | 4/1999 | Sagel et al. | |
| 5,989,569 A | 11/1999 | Dirksing et al. | |
| 6,045,811 A | 4/2000 | Dirksing et al. | |
| 6,343,932 B1 | 2/2002 | Wiesel | |
| 6,419,903 B1 | 7/2002 | Xu et al. | |
| 6,551,579 B2 | 4/2003 | Sagel et al. | |
| 6,582,708 B1 | 6/2003 | Sagel et al. | |
| 6,585,997 B2 | 7/2003 | Moro et al. | |
| 6,649,147 B1 | 11/2003 | Ye et al. | |
| 2002/0006388 A1 | 1/2002 | Sagel et al. | |
| 2002/0012685 A1 | 1/2002 | Sagel et al. | |
| 2002/0187112 A1 | 12/2002 | Xu et al. | |
| 2003/0008008 A1 | 1/2003 | Leung et al. | |
| 2003/0044361 A1 | 3/2003 | Chen | |
| 2003/0129148 A1 | 7/2003 | Chen | |
| 2003/0152528 A1 | 8/2003 | Singh et al. | |
| 2003/0194382 A1 | 10/2003 | Chang et al. | |
| 2003/0211056 A1 | 11/2003 | Sagel et al. | |
| 2003/0228264 A1 | 12/2003 | Perna | |
| 2004/0062724 A1 | 4/2004 | Moro et al. | |
| 2004/0086468 A1 | 5/2004 | Prosise et al. | |
| 2004/0105834 A1 | 6/2004 | Singh et al. | |
| 2004/0219113 A1 | 11/2004 | Choi et al. | |
| 2004/0247646 A1 | 12/2004 | Ivory et al. | |
| 2005/0276760 A1 | 12/2005 | Lokken | |

FOREIGN PATENT DOCUMENTS

CA        2500312        4/2004

*Primary Examiner* — Renee Claytor
(74) *Attorney, Agent, or Firm* — Vidas, Arrett & Steinkraus, P.A.

(57) ABSTRACT

A dissolving strip for tooth whitening the strip having at least a first tooth contacting layer and a second outer layer. The first tooth contacting layer has a solid tooth whitening active in an amount which reacts within a predetermined time when placed on a tooth. The second outer layer has a blend of polymers having different molecular weights; the blend of polymers being selected to dissolve after the predetermined time has elapsed. The outer layer contains the tooth whitening active on said tooth until the active is substantially used up. A method of forming a dissolving tooth whitening strip is also provided, in which the outer layer is formed on a backing layer followed by the inner layer being formed on the outer layer.

24 Claims, 3 Drawing Sheets

TOOTH WHITENING PRODUCTS AND METHODS OF MAKING THE SAME

CROSS-REFERENCE TO RELATED APPLICATIONS

This application is a Continuation of copending U.S. patent application Ser. No. 10/975064 filed Sep. 22, 2004, the entire content of which is incorporated by reference herein.

FIELD OF THE INVENTION

This invention relates generally to the field of cosmetic preparations and more particularly to products which may be used by individuals to whiten their teeth as well as relating to methods of making such tooth whitening products.

BACKGROUND OF THE INVENTION

Tooth whitening is becoming more common as improved tooth whitening technologies are developed. At present two forms of self applied tooth whitening procedures predominate. In one form, a formulation including a tooth whitening active is supplied on a thin flexible substrate or strip, which is then applied to the teeth. The flexible backing layer protects the active and permits the active to contact the teeth long enough to have a whitening affect. Typically the tooth whitening strip is left in contact with the teeth for about 30 minutes or more. The use of clear strips permits the user to be active during the teeth whitening procedure. However, once the tooth whitening step is complete, it is necessary to remove the remaining substrate and dispose of it, which is awkward. Examples of this type of tooth whitening product are found in the following patents:

U.S. Pat. No. 5,879,691 issued Mar. 9, 1999
U.S. Pat. No. 5,891,453 issued Apr. 6, 1999
U.S. Pat. No. 5,894,017 issued Apr. 13, 1999
U.S. Pat. No. 5,989,569 issued Nov. 23, 1999
U.S. Pat. No. 6,045,811 issued Apr. 4, 2000
U.S. Pat. App. No. 2002/0006388 published on Jan. 17, 2002
U.S. Pat. App. No. 2002/0012685 published on Jan. 31, 2002
U.S. Pat. App. No. 2002/0187112 published on Dec. 12, 2002
U.S. Pat. App. No. 2003/0044361 published on Mar. 6, 2003
U.S. Pat. No. 6,582,708 issued Jun. 24, 2003
U.S. Pat. App. No. 2003/0129148 published on Jul. 10, 2003
U.S. Pat. App. No. 2003/0194382 published on Oct. 16, 2003
U.S. Pat. App. No. 2003/0211056 published on Nov. 13, 2003

The second predominant form of tooth whitening is in the form of brush-on tooth whitening products. Brush-on products typically take the form of a viscous gel, which is packaged in a small bottle, with an accompanying brush-on applicator. Essentially what is required is to stretch the lips away from the teeth and brush on the gel, which includes a teeth whitening active. In order to be efficacious, the tooth whitening gel needs to adhere to the tooth surface and must be carefully applied only to the tooth enamel and not to any mucosal membrane such as the gums. The active requires the person applying the product to keep their mouth open and their soft tissue away from their teeth for a recommended amount of time, usually around 30 seconds. In brush-on tooth whitening products there is no barrier to protect the mucosal membranes after the lips are closed; this has the potential to both cause soft tissue irritation and displace whitening active from the tooth surface.

Physiologically acceptable consumable films are known including an antimicrobial effective amount of essential oils, as taught by U.S. Patent Application 2003/0008008. This patent application does not teach tooth whitening.

More recently, an erodible strip has been proposed as a means of carrying a tooth whitening active in the mouth. An example is disclosed in the U.S. application 2004/0062724 which is directed to an erodible film for treating the surfaces of teeth. This patent application discloses a thin flexible bi-layer or multi-layer of film which when applied to teeth surfaces adheres and delivers an active compound to the underlying surface. In the mouth the film erodes at a predetermined rate. The amount of time that the active agent remains in contact with the teeth surfaces is controlled by the rate of erosion of the backing layer, which is in turn controlled by the composition of the backing layer of the composite film. This application teaches that the erosion or residence time can be regulated one half hour to three hours depending on the desired therapeutic or cosmetic appearance. The erosion is controlled by use of at least one hydrophobic polymer or a combination of hydrophilic and hydrophobic polymers. However, having the film in contact with the teeth for such a long period of time makes use of the product awkward. More specifically during the time the film is in contact with the teeth the person may not be able to eat, drink or the like, for fear of affecting the tooth whitening process.

U.S. patent application 2003/0228264 discloses a tooth whitening strip made from a dissolvable matrix. The tooth whitening material may be contained in a pocket or mixed in with the dissolvable matrix. Various types of matrix are taught, but there is no teaching how to control the rate of dissolution of the matrix.

What is desired is a method of tooth whitening using a thin strip which is fast, easy to use and reliable, having a known and predetermined dissolution rate. Most preferably, such a tooth whitening system would enable teeth to be whitened by a predetermined amount in a period of up to approximately five minutes. After this time, the majority of tooth whitening active will be dissolved and the user will have little or no sensation of the product remaining in the mouth or on the tooth surface. Further, it is believed important that the manufacturing processes ensure that there is a viable amount of stable tooth whitening active provided.

SUMMARY OF THE INVENTION

According to one aspect the present invention provides a dissolving strip for tooth whitening having at least two layers. In this aspect of the invention the inner or tooth-contacting layer includes a solid tooth whitening active which adheres to the tooth surface. The tooth whitening active layer that is provided in an amount that reacts in a predetermined time. The second layer is provided with a controlled dissolution rate. In this invention the controlled dissolution rate is achieved by forming a relatively thin solid film by blending two or more polymers, having different molecular weights, to achieve the desired dissolution rate. What has been discovered is that the dissolution rate of the solid film can be controlled in part by the proportions of such polymers used to make the dissolvable film. The most preferred dissolution rate is to have the outer layer fully dissolved after the entire active is substantially used up in tooth whitening.

According to another aspect of the present invention a method is taught of making a solid dissolvable strip which reduces the amount of tooth whitening active that is lost or rendered unstable during the manufacturing process. In one embodiment the manufacturing involves forming a liquid solution/mixture which is then cast and dried to form the thin film. Typically however, tooth whitening actives will degrade upon exposure to water or heat. In this case, the present invention provides dissolving the active in a volatile solvent such as ethanol, to prevent the dissociation of hydrogen peroxide from the stabilizing agent (e.g. PVP), which would occur in a water based solution. As well, to limit the exposure of the active to heat, the solvents volatility will permit a shorter residence time in any drying step. In another embodiment the present invention provides that the active be applied in the form of a dry powder sprayed onto an outer layer or sprayed on to create an outer layer. In this case the spraying step may occur immediately after or during the drying step at a time when the outer layer is sufficiently tacky to permit the powdered spray to adhere thereto. In the present invention, the active layer is formed last, to reduce the time the active layer is exposed to the manufacturing environment. In this way higher effective amounts of tooth whitening active can be provided in the tooth contacting layer, meaning that more whitening can occur and or the whitening will take less time. This advantageously permits a thinner film and/or a more rapidly dissolving film to be used both of which are desirable to consumers.

BRIEF DESCRIPTION OF THE DRAWINGS

Reference will now be made to drawings which illustrate preferred embodiments, by way of example only, of the present invention and in which.

DETAILED DESCRIPTION OF THE PREFERRED EMBODIMENTS

Figure 1:
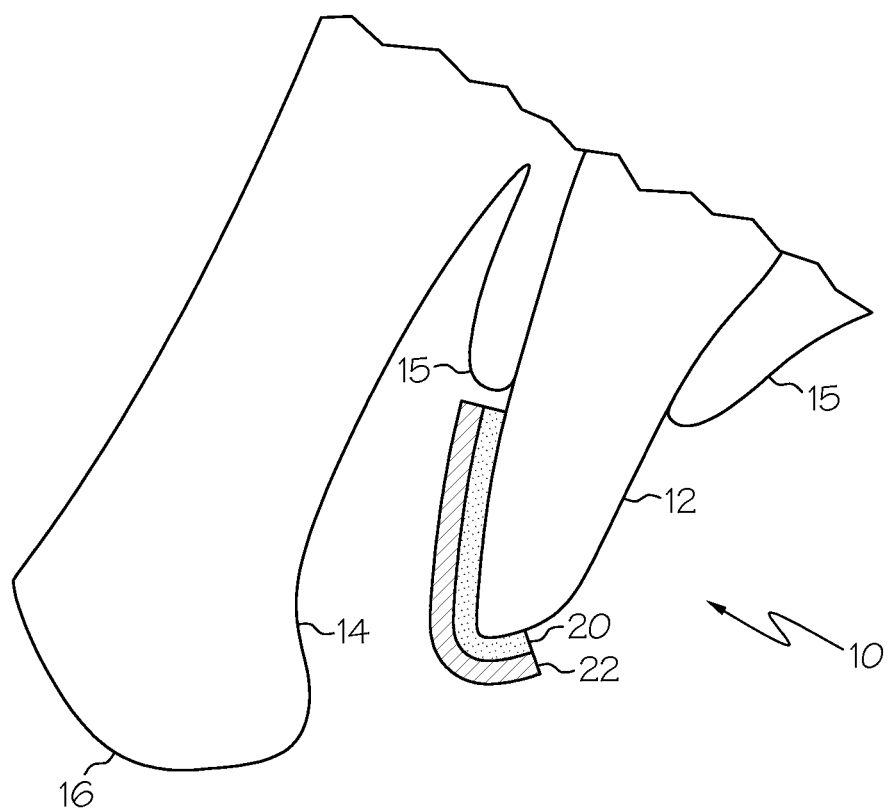
FIG. 1 is a view of a first embodiment of a dissolvable tooth-whitening strip according to the present invention in place on a tooth surface between a tooth surface and the lip.

The tooth whitening device is illustrated generally at 10 and is shown placed on a tooth 12 between the tooth 12 and an inner surface 14 of a lip 16. The inner surface 14 of the lip 16 is a mucosal membrane and is quite sensitive, as are the gums 15. The tooth surface 12 is a hard enamel surface, which is typically somewhat insensitive.

In the embodiment of FIG. 1 the present invention takes the form of a bi-layer dissolving tooth whitening strip. The bi-layer strip includes a first tooth surface contacting layer 20 and a second soft tissue or mucosal membrane contracting layer 22. The inner layer (tooth-side layer) 20 most preferable includes a solid tooth whitening agent, such as PVP-hydrogen peroxide. Where PVP-hydrogen peroxide is used, various molecular weight blends are preferred to assist in forming a readily castable material. For example, at least two molecular types are preferred, one with a low molecular weight, of at least 8,000 Daltons and most preferably around 60,000 Daltons and at least a second type with a molecular weight of less than 3,000,000 Daltons and most preferably about 1,300,000 Daltons. In the preferred form of the invention there is more of the low molecular weight type present than the high molecular weight type. Other forms of solid whitening agent suitable for the present invention include carbamide peroxide (urea peroxide), and other polymer resin bound hydrogen peroxides. Examples of other polymer resins are: PVP/MA (poly alkyl vinyl ether-maleic acid), PVP/MA copolymer, PVPNA (polyvinyl pyrrolidone-vinyl acetate), and PVPNA copolymer. Also, the polymer resins that contain bound hydrogen peroxide may be cross-linked, this would yield them water insoluble, and would therefore minimize or eliminate any peroxide dissociation when casting the inner layer which would subsequently improve peroxide concentration after completion of the manufacturing process.

Although various amounts of tooth whitening active can be used, it is preferred to have an amount of tooth whitening active that is substantially used up in a predetermined amount of time. The preferred amount if time is a matter of minutes, and a most preferred amount of time is under ten minutes, preferably between three and seven minutes and most preferably approximately five minutes. In this sense, substantially used up or reacted means that the tooth whitening active is sufficiently used up to avoid causing discomfort to the user of average sensitivity. Thus, while there may be some residual tooth whitening active left after the predetermined time, in general it is at a low enough level that the more sensitive lip and gum tissues which may come into contact with said residual active are not substantially adversely or uncomfortable affected.

It is preferred to maximize the weight percent of PVP-hydrogen peroxide in the tooth contacting layer, so that the maximum whitening effect can be achieved with the thinnest layer. Also since some tooth whitening active is lost during manufacturing or rendered less stable it is preferred to start with as much as possible, without needing a thicker film. Thus, it is preferred if the solid active is at least 80% dry weight to weight of the inner layer, more preferred to be over 90% and most preferred to be about 93%.

The inner layer 20 is preferable formed from a combination of solid peroxides and polyols such as propylene glycol and glycerine. These latter compounds act as plasticizers that add flexibility to the solid film to permit the solid film to be easily handled by the user and to permanently deform onto the rounded tooth surfaces.

According to the present invention the tooth whitening layer or inner layer 20 is preferably formed by dissolving the above-noted ingredients into a volatile solvent. In this sense a volatile solvent is any solvent that is readily vaporizable at a relatively low temperature and in any event is more readily vaporized than water and which does not readily dissociate the hydrogen peroxide from the polymer. A preferred solvent is 200 proof ethanol (anhydrous ethanol) that will not dissociate or minimize dissociation the hydrogen peroxide from the PVP. By using ethanol as the solvent the hydrogen peroxide remains bound to the PVP. In this manner more of the hydrogen peroxide is available for tooth whitening rather than being lost or rendered less stable in the manufacturing process. More hydrogen peroxide is available for two reasons: 1.) more hydrogen peroxide remains bound to the PVP or other polymer resin which increases yield at the end of the manufacturing process and, 2.) the evaporative properties of the ethanol minimize the time in the manufacturing process to increase hydrogen peroxide yield.

As noted above the present invention also comprehends using cross-linked polymers which are water insoluble in a water based mixture for casting, but since this will require a longer or more intense drying this is a less preferred embodiment. Such cross linked polymers may be formed into a mixture with water or solvent for casting proposes.

The solid dissolving outer layer 22 is primarily formed from hydroxypropylmethyl cellulose (HPMC). The outer layer 22 acts as a barrier layer to contain the active layer on the tooth surface until the active layer is substantially used up. Various additives are preferred for layer 22 including propylene glycol glycerin, and butylene glycol as plasticizers, citric acid, maltodextrin, colorants, sweeteners and flavoring agents. The sweetener may be a sugar free sweetener such as sucralose, potassium acesulfame and/or sodium saccharin, and the flavouring agents may be any preferred form of flavouring agents such as peppermint, spearmint, or the like. According to the present invention, the outer layer is formed by mixing the above-noted ingredients into water to form a solution, and then casting the solution in the form of a thin sheet onto a backing layer 23. By heat, vacuum, infrared or other drying, the water can be removed from the solution leaving as a residue a thin sheet material in the form of a solid, thin film.

Figure 2:
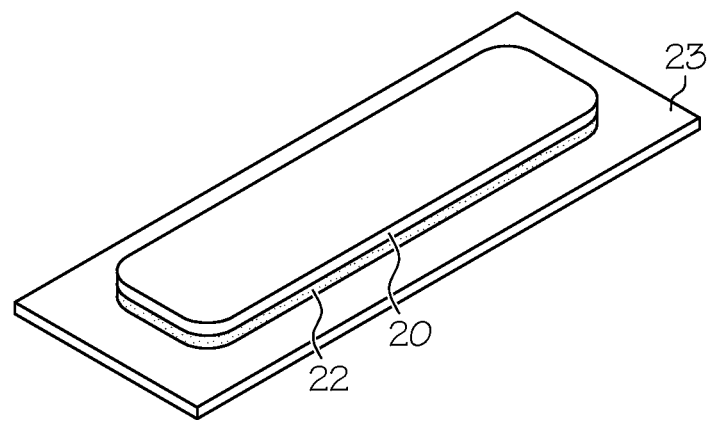
FIG. 2 is a view of the first embodiment of the invention on a backing strip.

FIG. 2 shows the bi-layer strip 10 on a backing strip 23. The removable backing strip 23 may be any form of any suitable material such as plastic, coated paper, or other material. The backing strip 23 should be flexible enough to be rolled into a roll, and impervious enough to have the wet solution cast onto it without penetrating the substrate. As well, the strip 23 needs to be smooth enough to permit the strip 23 and the outer layer 22 to be easily peeled apart when it is desired to apply the present invention to a tooth surface. It will now be understood that unlike some of the prior art the strip 23 of the present invention is not to be placed in the mouth and instead is removed and discarded before the tooth whitening strip of the present invention is placed in the mouth.

Figure 3:
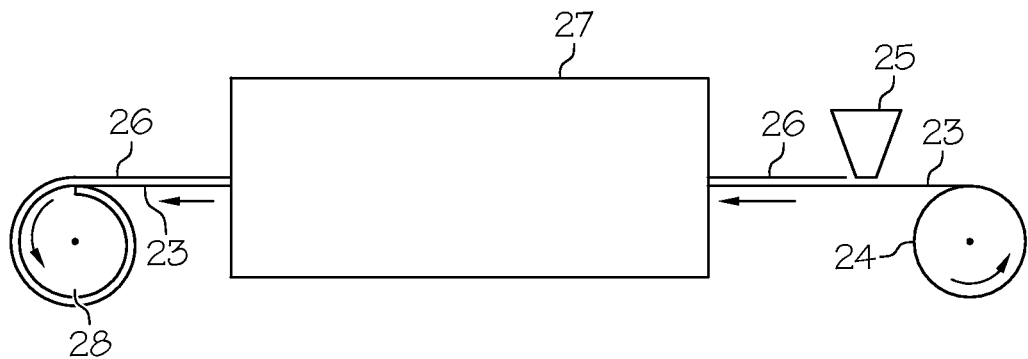
FIG. 3 is a view of a method of forming an outer layer of a dissolvable strip according to an aspect of the present invention.

The outer layer 22 is formed on the backing strip 23, by casting and drying as shown in FIG. 3. A feed roll 24 is wound with backing strip 23, and unwinds at a predetermined rate. A film casting apparatus 25 casts the water-based solution onto the backing strip 23 as a thin film 26. A drying tunnel 27 causes the water in the film 26 to evaporate, so that the film has less than 10% by w/w of water remaining, and is substantially solid. This permits the film 26 and backing strip 23 to be wound onto a take-up roll 28. The take up roll 28 must be unwound so the film must be dry enough to permit the winding and unwinding to occur. Then, the inner layer 20 can be cast onto the outer layer 22, and the volatile solvent, such as ethanol, is caused to rapidly evaporate from the inner layer to leave a second solid layer.

Figure 4:
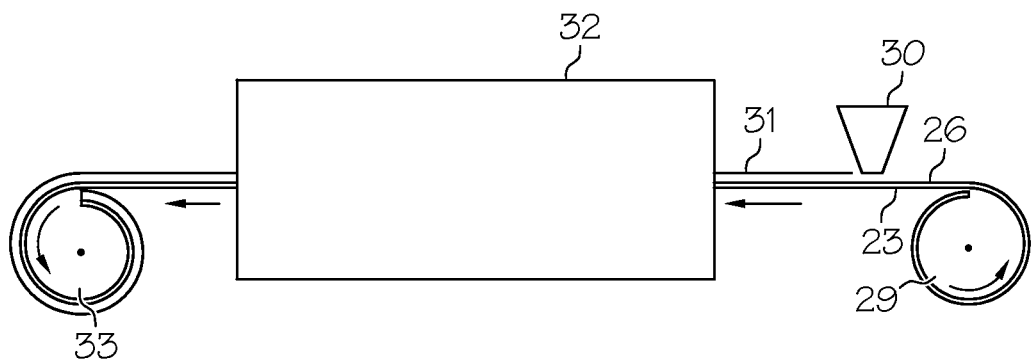
FIG. 4 is a view of a first method of forming a tooth-contacting layer of the dissolvable strip according to the present invention.

In FIG. 4, a feed roll 29 which includes the backing strip 23 and the film 26, unwinds to pass under a second film casting apparatus 30, which cast the solution of tooth whitening active and volatile solvent onto the film layer 26 to form a second layer 31. A further film drying apparatus 32 causes the ethanol to evaporate after which the two-layer film on the backing strip 23 is wound into a take-up roll 33. Again, the roll 33 will need to be unwound for further processing and packaging, so the second layer 31 needs to be dry enough to be wound without sticking. If further or other layers are desired, they can be cast in a like manner provided that, according to the present invention, the last layer formed contains the active.

In one form of the present invention the tooth contacting layer is cast wet onto the now dry outer layer. The wet solution is preferably a quick drying volatile solvent-based solution, rather than a water based solution. It is preferred to prevent the two layers from co-mingling too much. On the other hand it is also preferred if the two layers are securely joined together. It is most preferred to provide a wet enough solution, having regard to both the residence time of the solution on the outer layer before it is dried and the solubility of the outer layer in the solution, to permit enough of the outer layer to dissolve as the inner layer is cast onto the outer layer to form a bond between the inner and outer layers. Thus, according to the present invention in one embodiment the end product is a bi-layer strip with the PVP-hydrogen peroxide on the tooth contacting side and the HPMC barrier layer on the outer or lip contacting side.

The present invention provides that the outer layer be cast first onto the substrate and that the tooth whitening active layer be cast last. This has several advantages. More specifically the active is typically fairly reactive. Thus, to minimize the time the tooth active is vulnerable to being degraded, it is preferred to minimize the time the tooth whitening active is exposed to the manufacturing process. As noted above, the use of a volatile solvent allows the inner layer to be rapidly dried, as compared to a less volatile solvent such as water. The use of a non-dissociating solvent such as ethanol also tends to preserve the tooth whitening active.

Figure 5:
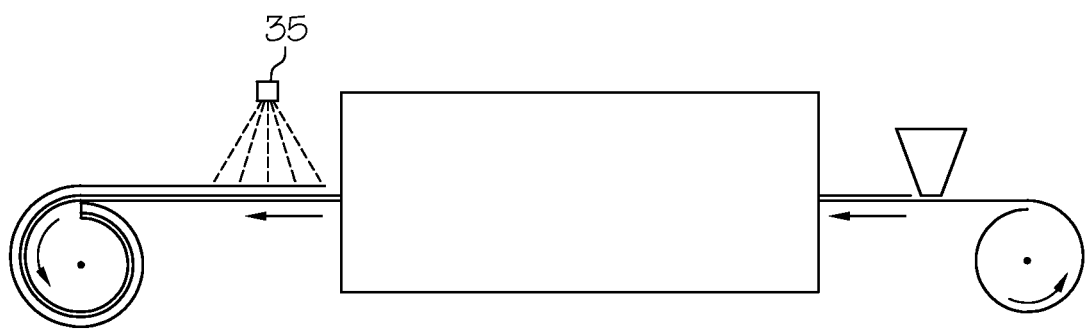
FIG. 5 is a view of a second method of forming a tooth-contacting layer of the dissolvable tooth-whitening strip according to the present invention.
Figure 6:
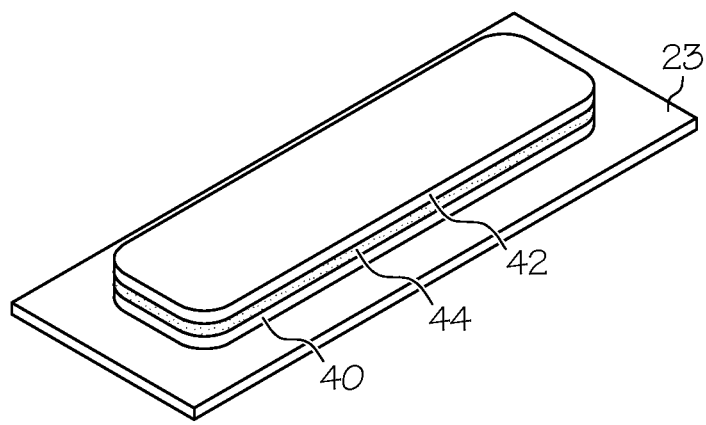
FIG. 6 is a view of a second embodiment of the dissolvable tooth-whitening strip on a backing strip.

The present invention also comprehends using tooth whitening actives which are not able to be wet cast onto the outer layer. For example, sodium chlorite is a tooth-whitening active that may also be used to form an inner or tooth-contacting layer. In this case it is preferred to spray the inner layer onto the outer layer as a dry powder spray. Most preferably the dry powder spray will be applied to the outer layer when the outer layer is still tacky enough to cause the inner layer to adhere thereto. This is shown in FIG. 5, where after the drying apparatus 27 a, a powder spray apparatus 35 is shown. In addition, or in the alternative, additives may be used in the powder to improve the adhesion of the dry powder to the outer layer. In the spray powder embodiment the bi-layer film can be formed in a single pass through the equipment from feed roller to take up roller which saves manufacturing time and cost.

The present invention further comprehends two component tooth-whitening systems, where one component is located in the inner layer and a second component is located in an adjacent layer. Thus, as the layers dissolve, the two components are brought together to enhance tooth whitening. In some cases the second component may simply be an accelerant and in other cases the second component may be required to produce the tooth whitening action. For example, in the embodiment of the present invention where the inner layer is sodium chlorite, it is most preferred to provide an acid agent or accidulent to the outer layer, to accelerate the tooth whitening reaction. Where the whitener is a form of peroxide, then an alkaline agent can be used as an accelerant.

The properties of the product in use can now be more fully discussed. According to the present invention, in use the HPMC is relatively rapidly dissolving and will most preferably dissolve within approximately five minutes of being applied. The PVP hydrogen peroxide, upon contacting a moistened tooth, demonstrates good adhesion to the tooth surface and once applied will keep the present invention in place on the teeth. Relatively high concentrations of PVP-hydrogen peroxide are desired in the inner layer in order that the whitening effect will occur more rapidly than the rate of dissolution of the outer layer. According to the present invention, it is most preferred if the PVP-hydrogen peroxide is substantially used up before the outer layer is completely dissolved. In this way, the PVP-hydrogen peroxide is prevented from causing any sensitivity or irritation on inner surface of the lip or on the gums.

Good results have been achieved with the PVP-hydrogen peroxide comprising over 90% by dry weight of the inner layer. In the manufacturing process by which the ethanol is evaporated under heat, some of the hydrogen peroxide becomes dissociated and is more susceptible to degradation during the manufacturing process. As will be understood by those skilled in the art, the theoretical hydrogen peroxide available from a 90% by weight PVP-hydrogen peroxide layer is approximately 18% to 20% of the inner layer. Due to degradation of tooth whitener which occurs during drying, this percentage is further reduced to approximately 5% w/w in the final product. Therefore, according to the present invention, the inner layer has a theoretical hydrogen peroxide content of approximately 10% w/w.

Turning now to the outer layer, most preferably the outer layer is comprised primarily of HPMC, with 40-80% dry weight of the outer layer. yielding good results. In order to have the HPMC outer layer dissolve at an appropriate rate, the present invention comprehends having the outer layer composed of a number of different molecular weights of HPMC. Good results have been achieved with a combination of HPMC having approximated molecular weights of 10,000 Daltons, 26,000 Daltons and 86,000 Daltons. It has been found that when all high molecular weight HPMC is used, the material does not dry or dissolve in an appropriate fashion. Similarly, if only a low molecular weight HPMC is used, the product does not have the right texture, dissolution time and rigidity. What has been found is that a combination of molecular weights is required in order to achieve a combination of desirable properties including an appropriate texture for mouth-feel, an appropriate drying time for manufacturing purposes, and an appropriate dissolution rate for controlled dissolving of the film in the mouth. Good results have been achieved with an approximate weight ratio of 4 parts 10,000 Dalton HPMC; 6 parts 26,000 Dalton HPMC; and 1 part 86,000 Dalton HPMC.

The present invention therefore seeks to optimize certain film qualities in a thin film. A thin film is preferred so that it is less noticeable in the mouth and feels less awkward to the user. A rapidly reacting tooth whitening active is preferred so that the entire strip may rapidly dissolve, while at the same time delivering an efficacious amount of tooth whitening before the strip is fully dissolved and containment of the active is lost. A slower dissolving strip will permit the active to be contained longer, for enhanced whitening. While some control over the dissolving time can be achieved through film thickness, this cannot be the only form of control, since an excessively thick film will be uncomfortable. What is desired is a thin strip which provides efficacious whitening without causing irritation or discomfort to the user. Reasonable results have been obtained where in a bilayer film where the film is between 0.05 mm and 0.5 mm thick, with about 0.15 mm being most preferred. A trilayer film is most preferably between 01.5 to 0.2 mm thick. In both films it is preferred if the outer layer is at least about one half of the overall thickness of the dissolving film strip.

In addition to the foregoing, other aspects of the present invention can now be understood. More particularly, the present invention comprehends adding to the outer layer an anti-tartar agent. Although the products such as the present invention achieve tooth whitening to reliable extent, recently whitened teeth tend to more easily stain than might otherwise be the case. Therefore, according to the present invention, providing an anti-tartar agent in the film counteracts this tendency. As the film dissolves, the anti-tartar agent is deposited onto the outer surface of the tooth that has been whitened. The anti-tartar agent(s), help prevent the calcification of bacterial plaque. Through this process, the fixing of staining bodies may be retarded, and subsequent use of whitening film may be more efficacious. Therefore, the present invention comprehends that an anti-tartar agents such as a polyphosphates, e.g. sodium tripolyphosphate, be included in the outer layer and that it would be distributed onto the teeth to provide anti-tartar protection to the newly whitened teeth.

Table 1 below shows various formulations of a bi-layer dissolvable tooth-whitening product according to the present invention.

| Bilayer Formulation Examples | | | | | | | | |
|---|---|---|---|---|---|---|---|---|
| Ingredient | % w/w (dry) | % w/w (dry) | % w/w (dry) | % w/w (dry) | % w/w (dry) | % w/w (dry) | % w/w (dry) | Phase |
| HPMC 5,000-10,000 Daltons | 14.80 | 14.80 | 11.10 | 7.40 | 14.80 | 22.20 | 22.20 | Outer Layer |
| HPMC 26,000 Daltons | 22.20 | 22.20 | 18.50 | 29.60 | 22.20 | 33.30 | 33.30 | |
| HPMC 86,000 Daltons | 3.70 | 3.70 | 11.10 | 3.70 | 3.70 | 5.55 | 5.55 | |
| Maltodextrin | 8.00 | 8.00 | 8.00 | 8.00 | 8.00 | 10.00 | 10.00 | |
| Citric Acid | 0.50 | 0.00 | 0.50 | 0.50 | 0.50 | 1.00 | 2.00 | |
| Sodium Hydroxide | 0.00 | 0.50 | 0.00 | 0.00 | 0.00 | 0.00 | 0.00 | |
| Propylene Glycol | 0.17 | 0.51 | 0.17 | 0.17 | 0.17 | 0.88 | 0.88 | |
| Glycerin | 0.17 | 0.00 | 0.17 | 0.17 | 0.17 | 0.00 | 0.00 | |
| Butylene Glycol | 0.17 | 0.00 | 0.17 | 0.17 | 0.17 | 0.00 | 0.00 | |
| Flavor | 0.50 | 0.50 | 0.50 | 0.50 | 0.50 | 0.50 | 0.50 | |
| Sodium Tripolyphosphate | 1.50 | 1.50 | 1.50 | 1.50 | 1.50 | 1.50 | 1.50 | |
| Sucralose | 0.07 | 0.07 | 0.07 | 0.07 | 0.07 | 0.07 | 0.07 | |
| Sodium Chlorite | 0.00 | 0.00 | 0.00 | 0.00 | 0.00 | 2.50 | 5.00 | Inner Layer |
| Urea Peroxide | 0.00 | 0.00 | 0.00 | 0.00 | 20.00 | 0.00 | 0.00 | |
| PVP-Hydrogen Peroxide | 35.50 | 35.50 | 35.50 | 35.50 | 0.00 | 0.00 | 0.00 | |
| PVP-Hydrogen Peroxide | 8.58 | 8.58 | 8.58 | 8.58 | 0.00 | 0.00 | 0.00 | |
| PVP | 0.00 | 0.00 | 0.00 | 0.00 | 24.08 | 22.50 | 19.00 | |
| Propylene Glycol | 2.25 | 2.25 | 2.25 | 2.25 | 2.25 | 0.00 | 0.00 | |
| Glycerin | 1.89 | 1.89 | 1.89 | 1.89 | 1.89 | 0.00 | 0.00 | |

-continued

Bilayer Formulation Examples

| Ingredient | % w/w (dry) | % w/w (dry) | % w/w (dry) | % w/w (dry) | % w/w (dry) | % w/w (dry) | % w/w (dry) | Phase |
|---|---|---|---|---|---|---|---|---|
| Total Dry % | 100.00 | 100.00 | 100.00 | 100.00 | 100.00 | 100.00 | 100.00 | |

FIG. 3 shows a second embodiment of the present invention in which an outer layer 40 and an inner layer 42 are disposed about a middle layer 44. According to this embodiment of the present invention, the outer layer 40 would be primarily HPMC and the inner layer 42 would include solid peroxide such as PVP-hydrogen peroxide to provide tooth whitening to the teeth. The middle layer 44 preferably includes the anti-tartar agent and is on a relatively quickly dissolving media such as PVP or low molecular weight HPMC. An accelerant may also be added to the middle layer to facilitate tooth whitening. According to the present invention, the inner layer 42 and the middle layer 44 should be dissolved slightly before the outer layer 40 dissolves. In this way, the tooth actives will be used up before the protection and containment of the active by the outer layer 40 is lost.

Table 2 below shows various formulations of a tri-layer dissolvable strip according to the present invention.

corners. It has been found that reasonable results can be achieved with a single shape for use on both the top and the bottom teeth. When the die cut is made to define the application shape, the backing strip is preferably not cut also. In the next step, the excess dissolving strip material is removed from the backing sheet. In this manner the edge of the dissolving strip to be applied to the teeth of the user stands proud of the backing sheet and is smaller in area than the backing sheet or substrate. This permits the backing sheet to be easily bent to cause the strip and the substrate to separate to permit the strip to be removed by hand from the backing sheet when it comes time to use the strip by applying it in a person's mouth.

Figure 7:
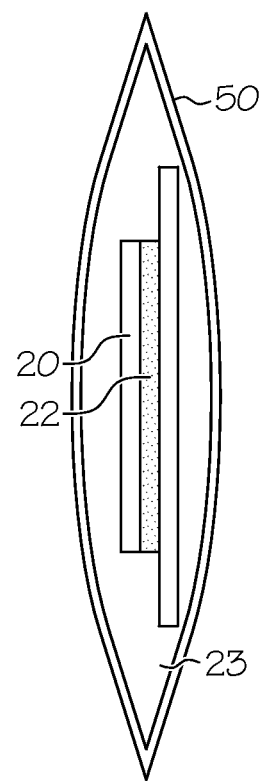
FIG. 7 is a view of an embodiment of the present invention in a pouch.

As shown in FIG. 7, most preferably the present invention is placed into an individual hermetically sealed and barrier coated pouch 50. The purpose of sealing the present invention is to preserve the whitening properties of the active, such as PVP-hydrogen peroxide over time.

Trilayer Formulation Examples

| Ingredient | % w/w (dry) | % w/w (dry) | % w/w (dry) | % w/w (dry) | % w/w (dry) | % w/w (dry) | % w/w (dry) | Phase |
|---|---|---|---|---|---|---|---|---|
| HPMC 5,000-10,000 Daltons | 7.40 | 7.40 | 5.55 | 3.70 | 7.40 | 11.10 | 11.10 | Outer |
| HPMC 26,000 Daltons | 11.10 | 11.10 | 9.25 | 14.80 | 11.10 | 16.65 | 16.65 | Layer |
| HPMC 86,000 Daltons | 1.85 | 1.85 | 5.55 | 1.85 | 1.85 | 2.78 | 2.78 | |
| Maltodextrin | 4.00 | 4.00 | 4.00 | 4.00 | 4.00 | 5.00 | 5.00 | |
| Citric Acid | 0.25 | 0.25 | 0.25 | 0.25 | 0.25 | 0.50 | 0.50 | |
| Sodium Hydroxide | 0.00 | 0.00 | 0.00 | 0.00 | 0.00 | 0.00 | 0.00 | |
| Propylene Glycol | 0.09 | 0.27 | 0.09 | 0.09 | 0.09 | 0.44 | 0.44 | |
| Glycerin | 0.09 | 0.00 | 0.09 | 0.90 | 0.09 | 0.00 | 0.00 | |
| Butylene Glycol | 0.09 | 0.00 | 0.09 | 0.09 | 0.09 | 0.00 | 0.00 | |
| Flavor | 0.50 | 0.50 | 0.50 | 0.50 | 0.50 | 0.50 | 0.50 | |
| Sodium Tripolyphosphate | 1.50 | 1.50 | 1.50 | 1.50 | 1.50 | 1.50 | 1.50 | |
| Sucralose | 0.07 | 0.07 | 0.07 | 0.07 | 0.07 | 0.07 | 0.07 | |
| HPMC 5,000-10,000 Daltons | 7.40 | 7.40 | 5.55 | 3.70 | 7.40 | 11.10 | 11.10 | Middle |
| HPMC 26,000 Daltons | 11.10 | 11.10 | 9.25 | 14.80 | 11.10 | 16.65 | 16.65 | Layer |
| HPMC 86,000 Daltons | 1.85 | 1.85 | 5.55 | 1.85 | 1.85 | 2.78 | 2.78 | |
| Propylene Glycol | 0.27 | 0.27 | 0.27 | 0.27 | 0.27 | 0.27 | 0.27 | |
| Citric Acid | 0.00 | 0.00 | 0.00 | 0.00 | 0.00 | 1.00 | 2.00 | |
| Sodium Hydroxide | 1.00 | 0.50 | 1.00 | 1.00 | 1.00 | 0.00 | 0.00 | |
| Maltodextrin | 3.22 | 3.72 | 3.22 | 2.41 | 3.22 | 4.66 | 4.66 | |
| Sodium Chlorite | 0.00 | 0.00 | 0.00 | 0.00 | 0.00 | 2.50 | 5.00 | Inner |
| Urea Peroxide | 0.00 | 0.00 | 0.00 | 0.00 | 20.00 | 0.00 | 0.00 | Layer |
| PVP-Hydrogen Peroxide | 35.50 | 35.50 | 35.50 | 35.50 | 0.00 | 0.00 | 0.00 | |
| PVP-Hydrogen Peroxide | 8.58 | 8.58 | 8.58 | 8.58 | 0.00 | 0.00 | 0.00 | |
| PVP | 0.00 | 0.00 | 0.00 | 0.00 | 24.08 | 22.50 | 19.00 | |
| Propylene Glycol | 2.25 | 2.25 | 2.25 | 2.25 | 2.25 | 0.00 | 0.00 | |
| Glycerin | 1.89 | 1.89 | 1.89 | 1.89 | 1.89 | 0.00 | 0.00 | |
| Total Dry % | 100.00 | 100.00 | 100.00 | 100.00 | 100.00 | 100.00 | 100.00 | |

As noted above a flexible bi-layer or multilayer film can be created on a flexible substrate that has sufficient flexibility and sheer strength to be rolled onto a large roll. The roll may then be transported to a slitting and packaging facility where the film is further processed into individual packages.

In the most preferred form of the present invention the roll is taken to a slitting station where it is slit to width and then cut to length. Thereafter, a die is applied to cut out the preferred shape of the tooth whitening strip. The most preferred dimensions are about 1.3 cm by 7 cm most preferably with rounded It can now be appreciated how the present invention is used by a person who wishes to whiten their teeth. First, a user would open the individual package to obtain a strip mounted onto a backing sheet or substrate for application to their teeth. Because the backing strip is the larger element they will tend to contact only the backing sheet at first. Then, they would remove the present invention from the backing strip by simply peeling away the backing strip. At this point, the film is soft, pliable and dry enough to easily handle. Then, the strip may be applied to the outer teeth and folded over onto the back side. Because of the adhesive properties of the PVP-hydrogen peroxide, the film will stay in place on the tooth. Thereafter, the person may close their lips and mouth and carry on in a normal manner. In any event, the present invention dissolves rather quickly and would be completely dissolved within approximately 5 minutes. The present invention can be used any time and therefore may be used once, twice or several times a day.

Because the present invention provides tooth whitening which is fast, convenient and easy to use, it may be self applied at any time during the day. Although it is preferred not to use the tooth whitening strip too often, the individual user can gauge the amount of whitening effect achieved and apply it more rapidly or more slowly as they desire. Because the active is contained by the outer layer until the active is substantially used up, multiple applications should not create irritation or sensitivity in the soft tissues of the mouth of a user of average sensitivity.

It will be appreciated by those skilled in the art that various modifications and alternations of the present invention can be made without departing from the scope of the claims that follow. Some of these modifications have been discussed above, and others will be understood by those skilled in the art.

I claim:

1. A tooth whitening product for a mouth having teeth and gums, the tooth whitening product comprising:
    a dissolving strip for tooth whitening, said strip comprising at least a first solid dissolvable tooth contacting layer, said tooth contacting layer comprising a tooth whitening active in an amount which reacts within a predetermined time when placed on a tooth;
    a dissolvable outer layer comprising a blend of polymers having different molecular weights, the blend of polymers being selected to dissolve after said predetermined dissolving time of said tooth contacting layer has elapsed, wherein said outer layer contains said tooth whitening active on said tooth and away from said gums until said active is substantially used up; and
    a bond formed between said tooth contacting layer and said outer layer by partially dissolving said tooth contacting layer into said outer layer when said tooth contacting layer is cast onto said outer layer.

2. A dissolving strip for tooth whitening as claimed in claim 1 wherein said dissolving strip is between 0.05 mm and 0.15 mm thick.

3. A dissolving strip for tooth whitening as claimed in claim 2 wherein said dissolving strip is about 0.15 mm thick.

4. A dissolving strip for tooth whitening as claimed in claim 2 wherein said outer layer dissolves in less than ten minutes.

5. A dissolving strip for tooth whitening as claimed in claim 1 wherein said outer layer dissolves in between three and seven minutes.

6. A dissolving strip for tooth whitening strip as claimed in claim 5 wherein said outer layer dissolves in about five minutes.

7. A dissolving strip for tooth whitening as claimed in claim 1 wherein said dissolving strip is mounted on a removable backing strip.

8. A dissolving strip for tooth whitening as claimed in claim 7 wherein said dissolving strip is mounted on said removable backing strip with said outer layer adjacent to said backing strip and said tooth contacting layer remote from said backing strip.

9. A dissolving strip as claimed in claim 1 wherein said outer layer contains one or more of a sweetener, a colorant and a flavouring agent.

10. A dissolving strip as claimed in claim 1 wherein said outer layer includes an anti-tartar active to be deposited on said tooth after said second outer layer dissolves.

11. A dissolving strip as claimed in claim 1 wherein said outer layer includes a tooth whitening accelerator, said tooth whitening accelerator combining with said tooth whitening active as said outer layer dissolves, said accelerator causing said tooth whitening active to react more quickly.

12. A dissolving strip as claimed in claim 1 wherein said first tooth contacting layer includes one or more plasticizers in an amount sufficient to render the first layer pliable enough to be placed on said tooth.

13. A dissolving strip as claimed in claim 12 wherein said plasticizers are selected from the group of polyols, glycerin, propylene glycol, butylene glycol and sorbitol.

14. A dissolving strip as claimed in claim 1 wherein said outer layer includes HPMC having at least three different molecular weights.

15. A dissolving strip as claimed in claim 14 wherein said HPMC includes a first HPMC type having a molecular weight of between 5,000 to 10,000 Daltons, a second HPMC type having a molecular weight of about 26,000 Daltons and a third HPMC type having a molecular weight of about 86,000 Daltons.

16. A dissolving strip as claimed in claim 15 wherein said first HPMC type has a dry weight to weight range of between 7.4 to 22%, said second HPMC type has a dry weight to weight range of between 18.5 to 33.3% and said third HPMV type has a dry weight to weight range of 3.7 to 11.1%.

17. A dissolving strip as claimed in claim 1 wherein said solid tooth whitening active in said tooth contacting layer is PVP-hydrogen peroxide.

18. A dissolving strip as claimed in claim 17 wherein said PVP-hydrogen peroxide tooth whitening active is at least 80% weight to weight dry of said tooth whitening layer.

19. A dissolving strip as claimed in claim 17 wherein said PVP-hydrogen peroxide tooth whitening active is at least 90% weight to weight dry of said tooth whitening layer.

20. A dissolving strip as claimed in claim 17 wherein said PVP-hydrogen peroxide tooth whitening active is about 93% weight to weight dry of said tooth whitening layer.

21. A dissolving strip as claimed in claim 17 wherein said PVP-hydrogen peroxide includes a first type of PVP-hydrogen peroxide having a low molecular weight of at least 8,000 Daltons and at least a second type of PVP-hydrogen peroxide having a higher molecular weight of no more than 3,000,000 Daltons.

22. A dissolving strip as claimed in claim 21 wherein said first type of PVP-hydrogen peroxide has a molecular weight of about 60,000 Daltons and at least a second type of PVP-hydrogen peroxide having a higher molecular weight of about 1,300,000 Daltons.

23. A dissolving strip as claimed in claim 21 wherein tooth contacting layer includes more of said first type of PVP-hydrogen peroxide than said second type of PVP-hydrogen peroxide.

24. A dissolving strip as claimed in claim 1 wherein said solid tooth whitening active in said tooth contacting layer is one or more of, a water insoluble cross linked PVP, carbamide peroxide, PVP/MA (poly alkyl vinyl ether-maleic acid), PVP/MA copolymer, PVP/VA (polyvinyl pyrrolidone-vinyl acetate), and PVP/VA copolymer.

* * * * *